US012697078B2

(12) United States Patent
Boxall et al.

(10) Patent No.: US 12,697,078 B2
(45) Date of Patent: Aug. 4, 2026

(54) PATIENT SUPPORT SYSTEM FOR USE WITH A MEDICAL DEVICE

(71) Applicant: Elekta Limited, Crawley (GB)

(72) Inventors: Paul Boxall, Crawley (GB); David Gilmore, Crawley (GB); Wayne Lomax, Crawley (GB)

(73) Assignee: Elekta Limited, Crawley (GB)

( * ) Notice: Subject to any disclaimer, the term of this patent is extended or adjusted under 35 U.S.C. 154(b) by 783 days.

(21) Appl. No.: 18/001,673

(22) PCT Filed: Mar. 31, 2021

(86) PCT No.: PCT/EP2021/058538
§ 371 (c)(1),
(2) Date: Dec. 13, 2022

(87) PCT Pub. No.: WO2022/002449
PCT Pub. Date: Jan. 6, 2022

(65) Prior Publication Data
US 2023/0329651 A1 Oct. 19, 2023

(30) Foreign Application Priority Data
Jun. 30, 2020 (GB) ...................................... 2010023

(51) Int. Cl.
*A61B 6/04* (2006.01)
*A61B 5/00* (2006.01)
(Continued)

(52) U.S. Cl.
CPC ............ *A61B 6/0407* (2013.01); *A61B 5/055* (2013.01); *A61B 5/704* (2013.01); *A61B 6/102* (2013.01);
(Continued)

(58) Field of Classification Search
CPC ......... A61B 6/0407; A61B 6/04; A61B 6/102; A61B 6/465; A61B 6/467; A61B 6/461;
(Continued)

(56) References Cited

U.S. PATENT DOCUMENTS

| | | | |
|---|---|---|---|
| 7,690,059 B2* | 4/2010 | Lemire | A61G 7/005 |
| | | | 5/616 |
| 7,779,493 B2* | 8/2010 | Lemire | A61G 7/0506 |
| | | | 5/616 |

(Continued)

FOREIGN PATENT DOCUMENTS

| | | | | |
|---|---|---|---|---|
| CN | 116194046 A | * | 5/2023 | A61N 5/1048 |
| DE | 102014214993 A1 | | 2/2016 | |

(Continued)

OTHER PUBLICATIONS

"International Application Serial No. PCT/EP2021/058538, International Search Report dated Jul. 6, 2021", (Jul. 6, 2021), 3 pgs.
(Continued)

*Primary Examiner* — Robert G Santos
(74) *Attorney, Agent, or Firm* — Schwegman Lundberg & Woessner, P.A.

(57) ABSTRACT
A patient support system for use with a medical device. The patient support system comprises a patient support surface comprising at least one electronic display region configured to display information; one or more proximity sensors configured to provide signals indicative of the presence of a person or object in the vicinity of the patient support surface; and a controller configured to control the information displayed on the at least one electronic display region based on signals received from the one or more proximity sensors.

24 Claims, 4 Drawing Sheets

(51) Int. Cl.
   *A61B 5/055*  (2006.01)
   *A61B 6/10*  (2006.01)
   *A61B 6/46*  (2024.01)
(52) U.S. Cl.
   CPC .............. *A61B 6/465* (2013.01); *A61B 6/467* (2013.01); *A61B 6/04* (2013.01); *A61B 6/461* (2013.01)
(58) Field of Classification Search
   CPC .... A61B 5/055; A61B 5/704; A61G 2203/30; A61G 2203/40
   USPC .............................. 5/601, 600, 905; 378/209
   See application file for complete search history.

(56)                References Cited

U.S. PATENT DOCUMENTS

| | | | | | |
|---|---|---|---|---|---|
| 7,805,784 | B2 * | 10/2010 | Lemire | ................ | A61G 7/0506 108/147 |
| 7,861,334 | B2 * | 1/2011 | Lemire | ................ | A61G 7/0507 5/280 |
| 7,962,981 | B2 * | 6/2011 | Lemire | ................... | B60T 17/22 5/616 |
| 8,393,026 | B2 * | 3/2013 | Dionne | ................... | A61G 7/08 340/686.1 |
| 8,701,229 | B2 * | 4/2014 | Lemire | ................. | A61G 7/005 5/510 |
| 9,126,571 | B2 * | 9/2015 | Lemire | .............. | A61M 5/1415 |
| 9,358,405 | B2 * | 6/2016 | Morris | ................... | A61G 13/02 |
| 9,539,156 | B2 * | 1/2017 | Lemire | ................... | B60T 7/085 |
| 9,555,778 | B2 * | 1/2017 | Lemire | ................... | B60T 17/22 |
| 9,815,439 | B2 * | 11/2017 | Lemire | ................... | A61G 7/012 |
| 10,410,500 | B2 * | 9/2019 | Derenne | ............. | A61B 5/7445 |
| 10,811,136 | B2 * | 10/2020 | Bhimavarapu | .... | G06Q 10/0639 |
| 11,627,927 | B2 * | 4/2023 | Hoecht | ................ | A61B 6/0407 700/83 |
| 11,710,556 | B2 * | 7/2023 | Bhimavarapu | .... | G06Q 10/0639 705/2 |
| 2007/0130692 | A1 | 6/2007 | Lemire et al. | | |
| 2007/0157385 | A1 * | 7/2007 | Lemire | ................ | A61G 7/0524 5/618 |
| 2007/0163043 | A1 * | 7/2007 | Lemire | ................ | A61G 7/0516 5/618 |
| 2007/0169268 | A1 * | 7/2007 | Lemire | ................... | A61G 7/015 5/617 |
| 2007/0174964 | A1 * | 8/2007 | Lemire | ................ | A61G 7/0528 5/430 |
| 2011/0162141 | A1 * | 7/2011 | Lemire | ................... | A61G 7/015 188/1.12 |
| 2011/0231996 | A1 * | 9/2011 | Lemire | ................... | A61G 7/052 5/613 |
| 2011/0277242 | A1 * | 11/2011 | Dionne | ................ | A61G 7/0524 5/613 |
| 2014/0059768 | A1 * | 3/2014 | Lemire | ................ | A61G 7/0527 5/611 |
| 2014/0237721 | A1 * | 8/2014 | Lemire | ................ | A61G 7/1046 188/1.12 |
| 2015/0077534 | A1 * | 3/2015 | Derenne | .............. | G06F 3/0416 348/77 |
| 2015/0151139 | A1 | 6/2015 | Morris et al. | | |
| 2016/0287459 | A1 * | 10/2016 | Lemire | .............. | A61M 5/1415 |
| 2018/0374573 | A1 * | 12/2018 | Bhimavarapu | ........ | G16H 40/20 |
| 2020/0129134 | A1 | 4/2020 | Hoecht et al. | | |
| 2020/0411175 | A1 * | 12/2020 | Bhimavarapu | ........ | G16H 40/63 |
| 2023/0329651 | A1 * | 10/2023 | Boxall | ................... | A61B 6/102 |

FOREIGN PATENT DOCUMENTS

| | | | | |
|---|---|---|---|---|
| WO | WO-2016195684 | A1 | 12/2016 | |
| WO | WO-2022002449 | A1 * | 1/2022 | ........... A61N 5/1048 |

OTHER PUBLICATIONS

"International Application Serial No. PCT/EP2021/058538, Written Opinion dated Jul. 6, 2021", (Jul. 6, 2021), 8 pgs.
"United Kingdom Application Serial No. 2010023.6, Examination Report dated Dec. 17, 2020", (Dec. 17, 2020), 6 pgs.
"Chinese Application No. 202180046978.X, Office Action dated Jul. 30, 2025", w English Translation, (Jul. 30, 2025), 12 pgs.
"United Kingdom GB2010023.6, Examination Report under Section 18(3) dated Jan. 31, 2023", (Jan. 31, 2023), 3 pgs.
"European Application No. 21 716 376.5, Communication pursuant to Article 94(3) EPC dated Apr. 3, 2025", (Apr. 3, 2025), 3 pgs.
"Chinese Application No. 202180046978.X, Office Action dated Feb. 11, 2026", w English Translation, Feb. 11, 2026, 8 pgs.

* cited by examiner

100

116

102

118

104

106

108

112

114

110

304

306

301

218

114

PATIENT SUPPORT SYSTEM FOR USE WITH A MEDICAL DEVICE

PRIORITY APPLICATIONS

This application is a U.S. National Stage Filing under 35 U.S.C. § 371 from International Application No. PCT/EP2021/058538, filed on Mar. 31, 2021, and published as WO2022/002449 on Jan. 6, 2022, which claims the benefit of priority to United Kingdom Application No. 2010023.6, filed on Jun. 30, 2020; the benefit of priority of each of which is hereby claimed herein, and which applications and publication are hereby incorporated herein by reference in their entireties.

This disclosure relates to a patient support system for use with a medical device.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour. Additionally, magnetic resonance (MR) imaging can be performed before and during treatment. A patient lies on a patient support surface and is patient movement is minimised to ensure the treatment area remains stationary. A medical operative controlling the procedure must therefore control multiple variables before and during treatment.

In existing systems, the operative has to shift between multiple locations and vary operation accordingly which is inefficient and disrupts clinical workflow.

The invention is set out in the claims.

SUMMARY

In an implementation there is provided a patient support system for use with a medical device, the patient support surface comprising: a patient support surface comprising at least one electronic display region configured to display information; one or more proximity sensors configured to provide signals indicative of the presence of a person or object in the vicinity of the patient support surface; and a controller configured to control the information displayed on the at least one electronic display region based on signals received from the one or more proximity sensors.

The proximity sensor may be a sensor configured to detect the presence of an object without physical contact.

Optionally the at least one electronic display region comprises a plurality of electronic display regions. The controller may be further configured to determine, based on the signals received from the one or more proximity sensors, which electronic display region of the plurality of electronic display regions is nearest the person or object in the vicinity of the patient support surface; and control the information displayed on the at least one electronic display region based on the determination.

Optionally the controller is further configured to display information only on the determined electronic display region.

Optionally the controller is further configured to deactivate the electronic display region if there is no signal indicative of presence.

Optionally the sensors are configured to identify an authorised person or object and provide signals indicative thereof or responsive thereto.

Optionally controller is further configured to display error or fault information.

Optionally the controller is configured to display information at the location where an action is to be performed.

Optionally the controller is configured to display information based on the next step in at least one of a clinical, service or physics workflow. The next step may comprise performing a step in relation to the patient support surface and wherein the displayed information indicates or is displayed at the location where the next step requires performance. The next step may comprise attaching an accessory to the patient support surface via one or more attachment features located on the patient support surface, and wherein the displayed information indicates the location of the one or more attachment features. The next step may comprise indicating via the electronic display region, patient positioning information.

Optionally the controller is further configured to control at least one of an MR imaging apparatus, an RT apparatus and a subject support surface.

Optionally the electronic display region further comprises an input interface. The input interface may comprise at least one of a touch screen, microphone or keyboard.

Optionally the controller is configured to receive, via the interface, an indication of the location of an imaging window and adjust, based on the imaging window, the position of the patient support surface. The indication may be the longitudinal location of two edges of the imaging window on the patient support surface.

Optionally the controller is configured to receive, via the interface, the location of a first edge of an imaging window, and display, on the display, a range for the second edge of the imaging window based on predetermined imaging window parameters. The controller is further configured to receive, via the input, the location of a second edge of an imaging window, the location being within the range.

Optionally the patient support system further includes an identification element detector configured to detect at least one of proximity and location of an identification element.

Optionally at least one of the at least one electronic display region, one or more proximity sensors, and/or controller are configured to deactivate in case of predetermined operator absence.

Optionally the controller is configured to update movement trajectory of a component of the radiotherapy device based on signals indicative of the presence of a person or object in the vicinity of the patient support surface from the proximity sensors. The controller may: determine that a component of the radiotherapy device will move to a location within a threshold distance of the person or object, and, update planned movement of the component to avoid the person or object. Optionally the controller may halt movement of the components of the radiotherapy device based on the detected object. Optionally the component is the patient support surface.

According to an implementation there is provided a method of controlling a patient support system electronic display region comprising receiving a signal from a proximity sensor, the signal being indicative of the presence of a person or object in the vicinity of the patient support surface; and controlling the information displayed on the at least one electronic display region based on signals received from the one or more proximity sensors.

The proximity sensor may be a sensor configured to detect the presence of an object without physical contact.

Optionally the method comprises displaying information in the vicinity of a detected person or object.

Optionally the method comprises deactivating the electronic display region when person or object presence is not sensed.

Optionally the method comprises displaying information in the electronic display region relating to a next step in a clinical workflow.

Optionally the method comprises indicating, at an area of the electronic display region adjacent a location for addition of an accessory, instructions or other indications in relation to attaching the accessory.

Optionally the method comprises controlling operation of at least one of an MR imaging apparatus, an RT apparatus and a subject support surface via the electronic display region.

Optionally the method comprises receiving, via the interface, an indication of the location of an imaging window and adjusting, based on the imaging window, the position of the patient support surface. The indication may be the longitudinal location of two edges of the imaging widow on the patient support surface.

Optionally the method comprises receiving, via the interface, the location of a first edge of an imaging window, and displaying, on the display, a range for the second edge of the imaging window based on predetermined imaging window parameters. The method further comprises receiving, via the input, the location of a second edge of an imaging window, the location being within the range.

According to an implementation there is provided a computer readable medium configured to execute instructions to perform the methods disclosed herein.

FIGURES

Specific embodiments are now described, by way of example only, with reference to the drawings, in which.

OVERVIEW

In overview the present invention relates to a patient support system, for example a table for use with a medical device such as a radiotherapy device having an electronic display region configured to display information. For example, the electronic display region can comprise a graphical user interface (GUI) provided around the edge of the table. The system further includes one or more proximity sensors which detect the approach of a user or operative such as a medical professional. The system also includes a controller configured to control the information on the GUI based on signals received from the proximity sensors. For example, the GUI can become active when the user approaches and/or can activate close to where the user is, leaving the rest of the GUI blank and inactive. Similarly, when the user moves away from the table the entire display can become blank and inactive. Further still, the display can be configured such that the GUI can provide medical operative-relevant information such as indication of set up positions on the table, next steps in medical workflow and so forth. Furthermore, the GUI can indicate an error or fault in the system in any appropriate manner such as by generating an alarm colour.

DETAILED DESCRIPTION

Figure 1:
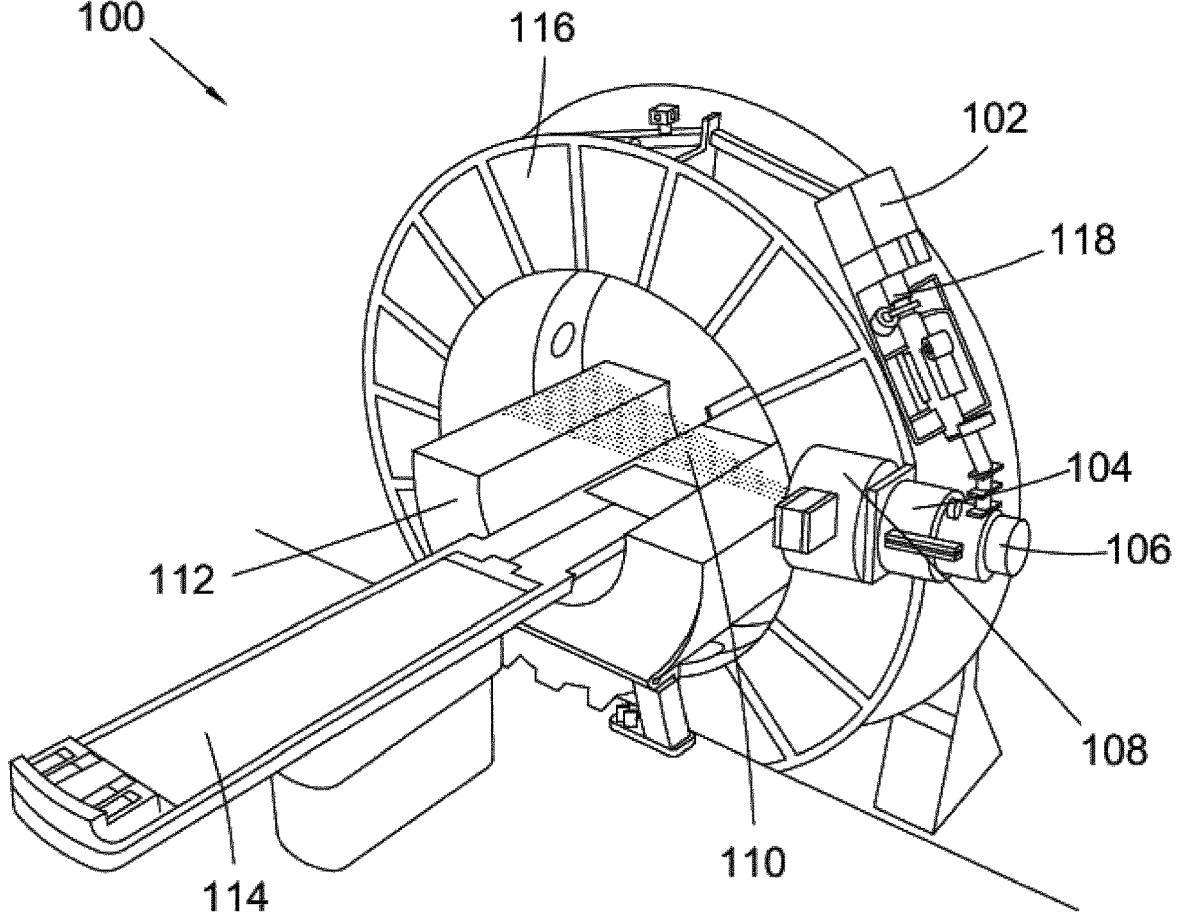
FIG. 1 depicts a radiotherapy device or apparatus according to the present disclosure.

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device comprises both MR imaging apparatus 112 and radiotherapy (RT) apparatus which may comprise a linac device. The MR imaging apparatus is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital. The skilled reader will be familiar with suitable MR and linac devices such that detailed description is not required here.

The MR-linac device depicted in FIG. 1 comprises a source of radiofrequency waves 102, a waveguide 104a source of radiation 106, a collimator 108 such as a multi-leaf collimator configured to collimate and shape the beam 110, MR imaging apparatus 112, and a patient support surface 114. In use the device would also comprise a housing (not shown) which, together with the ring-shaped gantry defines a bore. The moveable support surface 114 can be used to move a patient, or other subject, into the bore when an MR scan and/or when radiotherapy is to commence. The MR imaging apparatus 112, RT apparatus 120, and a subject support surface actuator are communicatively coupled to a controller or processor. The controller is also communicatively coupled to a memory device comprising computer-executable instructions which may be executed by the controller.

The radiation source 106 may comprise a beam generation system. For a linac, the beam generation system may comprise a source of RF energy 102, an electron gun, a circulator 118 and a waveguide 104. The radiation source is attached to the rotatable gantry 116 so as to rotate with the gantry 116. In this way, the radiation source 106 is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source of radiation 106 is configured to direct the beam 110 of therapeutic radiation toward a patient positioned on the patient support surface 114. The source of radiation 106 may comprise a heavy metal target toward which the high energy electrons exiting the waveguide are directed. When the electrons strike the target, X-rays are produced and collimated by collimator 108.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 112; an RT apparatus processor, which controls the operation of the RT apparatus; and a subject support surface processor which controls the operation and actuation of the subject support surface. The controller is communicatively coupled to a memory, i.e. a computer readable medium.

The linac device also comprises several other components and systems as will be understood by the skilled person. For example, in order to ensure the linac does not leak radiation, appropriate shielding is also provided.

Figure 2:
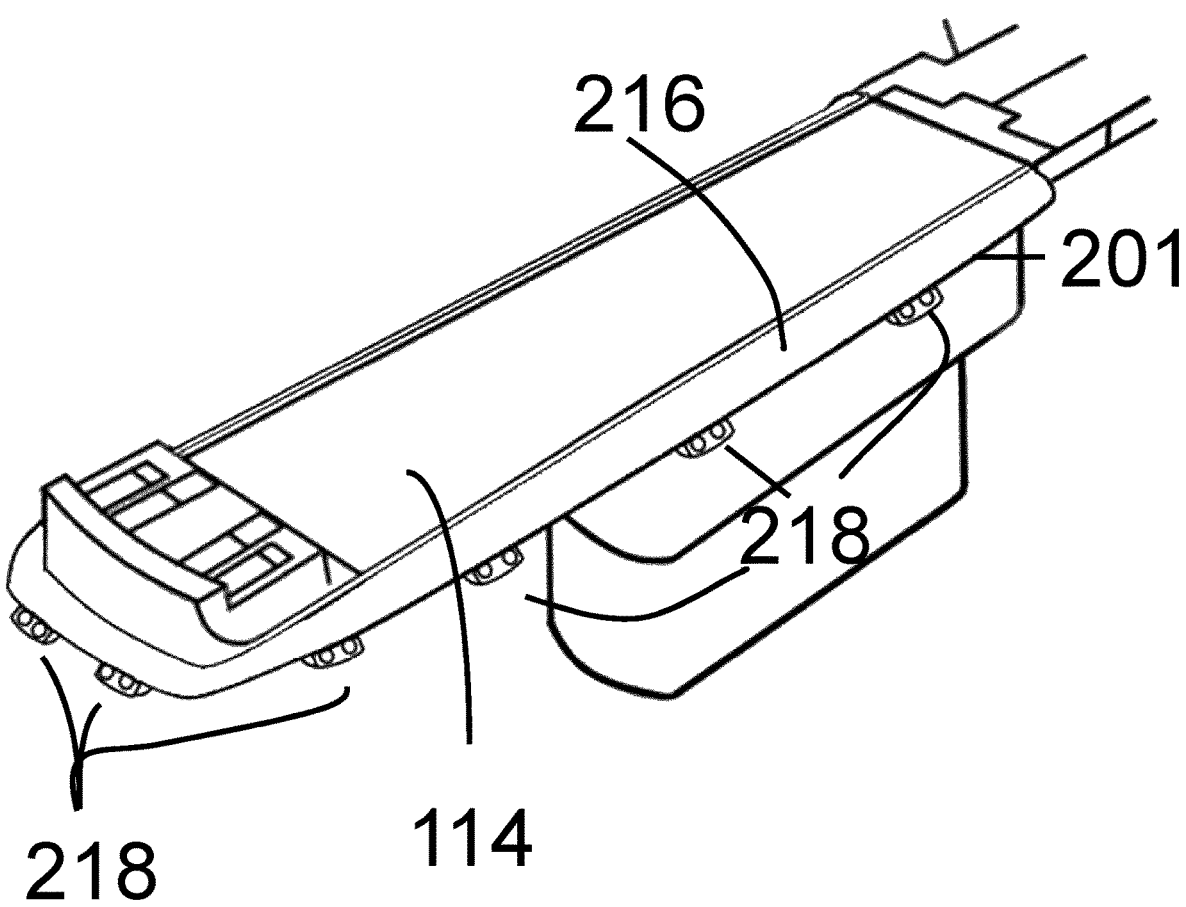
FIG. 2 depicts a radiotherapy device according to an embodiment of the present invention.

An embodiment of the invention will now be described with reference to FIG. 2. A patient support surface 114 includes an electronic display region 216 comprising a GUI provided around the edge of the table. Additionally, sensors 218 are provided around the periphery of the table (only those shown on two sides are visible in FIG. 2) as a result of which as a user approaches, the GUI can become active. It will be noted that in other embodiments the GUI is simply or additionally touch activated or otherwise activated to permit the user, such a medical operative, to access the information required. Any appropriate form of sensor can be incorporated, providing one or more of proximity, optical, infra-red, touch, acoustic, capacitative or any other relevant type of sensor. Of course, the sensors and other device components will of a type rated or able to withstand the radiation and other operating environment. Suitable component and other sensor types are known to the skilled reader and will not be presented in detail here. Additionally, the control environment can be modified to ensure that the radiation hardness of the displays, controller and other components is taken into account, for example by deactivating them when non-use is detected (for example the operative leaving the room, optionally in conjunction with the door being closed).

The terms user, operator and operative are used interchangeably in this disclosure.

Figure 3A:
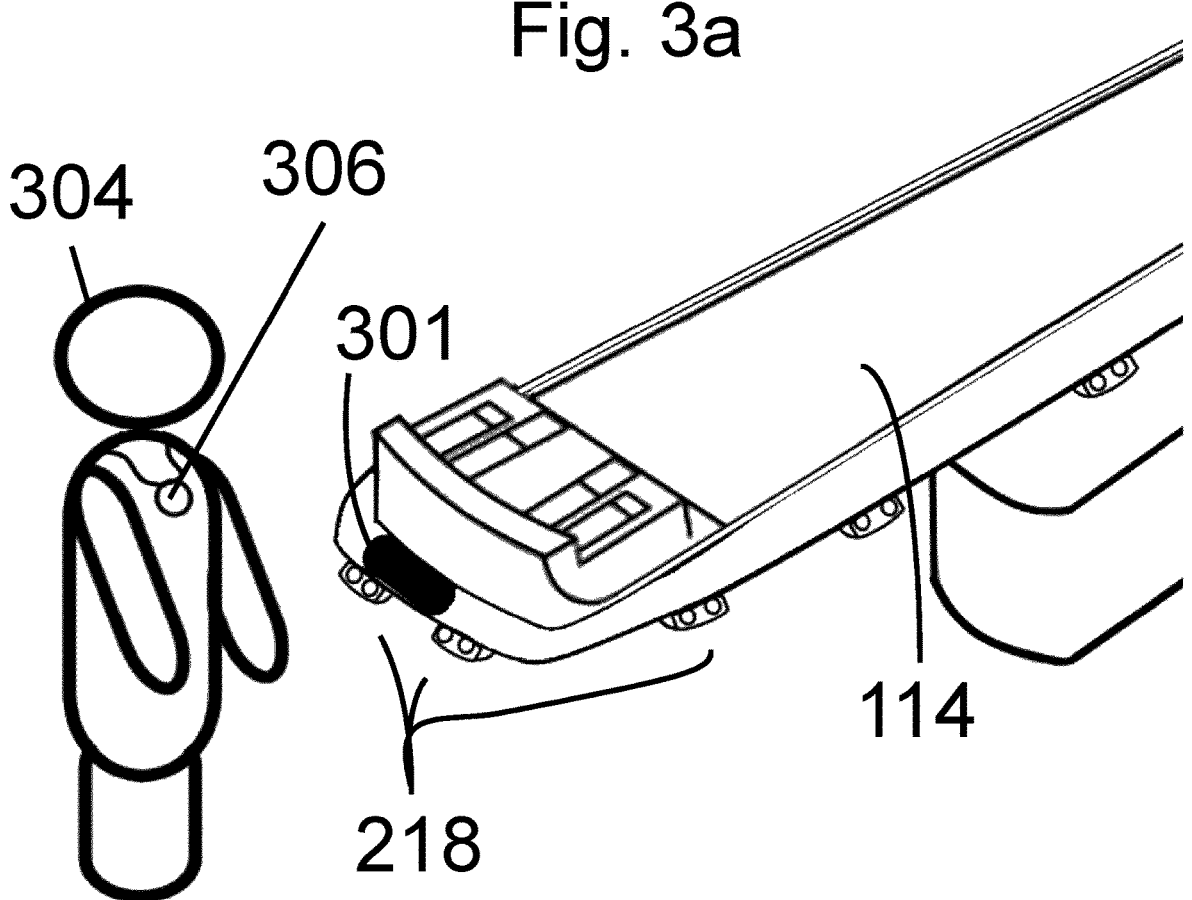
FIG. 3a and FIG. 3b depict operation of the radiotherapy device according to an embodiment of the present invention.

In instances where sensors 218 are activated by operative proximity, the GUI can activate in the vicinity of the operative as shown in FIG. 3*a*. In particular, a portion 301 of GUI 201 adjacent operative 304 is shown activated. Operative detection can be in any appropriate manner such as infrared or other proximity sensing, or sensing of an element carried by the operative such as a short distance communication pendant 306. In order to reduce power consumption and/or maintain simplicity of use, the remainder of the GUI can remain blank and inactive while the operative is not present.

A proximity sensor is a sensor configured to detect the presence of a nearby object without any physical contact with that object. A proximity sensor can be configured to detect the presence of an object within an area or zone, for example in the present disclosure within a radius or distance from the patient support surface. In some examples the detection zone may include the area to the side of the patient support surface (rather than above or below) to detect the presence of a user approaching the table from the side.

In some examples the sensors are configured to detect the presence of an object in a predetermined threshold distance from the table. The distance may be adjusted, selected or set by a user. The distance may be any conceivable distance chosen based on the configuration of the area surrounding the radiotherapy device. For example, the sensor may be configured to detect the presence of an objection within any of: 3 meters of the table, 2 meters of the table, 1.5 meters of the table, 1 meters of the table, 50 centimetres of the table etc.

Additionally, the sensors 118 can be activated by predetermined subject activity, for examples in case of emergency. To the extent the subject is mobile, waving or other alarm-indicating actions can be detected by sensors 118 as an indication of an alarm condition, triggering appropriate mitigation activity by the operative or controller. In one instance the sensors can be trained to distinguish between alarm-indicating movements and other subject movements by suitable gesture-detection software able to identify, for example, vigorous waving versus normal movement. The sensors 118 may detect additional or alternative alarm-indicating actions such as repeated tapping, with appropriate sensing technology (optical or touch or acoustic sensing capability). The sensing capability may be built into the existing proximity sensors or additional sensors 118 may be provided.

The GUI can comprise a controller for multiple components of the radio therapy device, for example an MR imaging apparatus controller, a radiotherapy apparatus controller or a subject support surface controller.

When the operative moves away, this is once again detected by the sensors 118 or otherwise such that the display can deactivate and go blank in those circumstances.

In some examples the GUI is calibrated to the table itself, meaning that location information for areas of the table can be indicated on the table itself. The GUI aligns with the location on the table, such that information can be displayed indicative of or at the location on the table. The GUI can display information and receive input based on the position on the table top itself, as explained in the examples below. The table can be used for a number of location indication means, including to show where accessories should go, where the patient's head should be, and also allow the user to select or mark a position on the table.

Figure 3B:
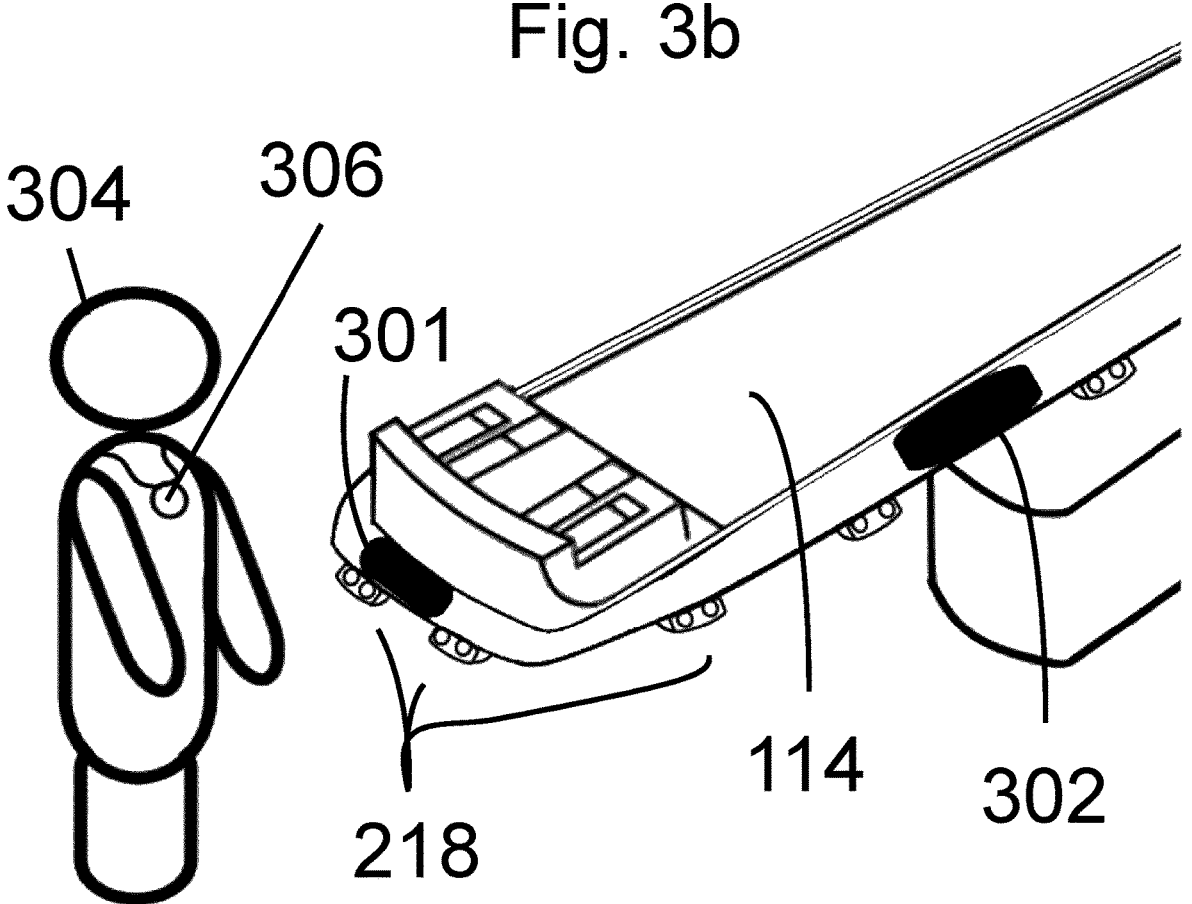

In one embodiment the GUI indicates set up positions on the table as shown in FIG. 3b. In particular, in addition to the highlighted area adjacent the operative 301, an additional area 302 is highlighted on the GUI remote from the operative. This can signify, for example, when and where operational elements need to be performed. As a result, the GUI provides additional guidance and awareness of clinical workflow.

For example, this can improve usage of radiation patient positioning functionality. The patient may need to be maintained in a fixed and defined position over a course of radiotherapy treatment, meaning that patient positioning accessories can be provided to help the patient maintain the defined position with comfort. Such accessories include couch tops and overlays, an immobilisation system, headrests, cushions, spaces and wedges, arm and wrist supports, thermoplastic masks and sheets, locating and indexing bars, bite positioners, markers, knee crutches, arm board/couch width extenders and so forth. When the next step comprises attaching such an accessory to the patient support surface for example via one or more attachment features located on the patient support surface, the displayed information on the GUI can indicate the location of the one or more attachment features and can, optionally, provide additional information as to how the attachment should be performed by virtue of written, animated, audible or other instructions.

The GUI can provide any appropriate information to the operative including, additionally, operation information, current performance, other instructions as to use, other communication messages, or error conditions: for example the entire GUI can go red as an alarm colour or otherwise indicate a fault in the system and can additionally light up adjacent portions to indicate where those problems are together with carrying corresponding information. It can also, of course, carry an input interface such as a touch screen, microphone, keyboard or other appropriate mechanism to permit the use to input information into the GUI to provide additional status information, seek assistance or guidance, or otherwise control components of the radiotherapy device.

The GUI can also direct usage during other phases of the MR operation. In one example, during servicing the GUI can permit service personnel interaction including providing service workflow guidance, directing personnel for example by illuminating areas experiencing problems or near problem locations, or by presenting relevant instructions in the vicinity of the service personnel. Similarly, during set up, testing, calibration or other non-clinical phases, the radiotherapist or physicist can be directed as discussed above by the GUI, for example during a physics workflow.

In one example the GUI could be used to define the imaging window and region of interest longitudinally for the patent on the table. In examples where the GUI is located along the longitudinal edge of the table, the user selects two points on the GUI along the edge of the table to mark either edge of the imaging window. The imaging window represents the bounds of an area for imaging before or during the radiotherapy procedure. In examples the GUI is a touch-screen.

The indication can be at the location of the edge of the imaging window, or aligned with the edge of the imaging window.

In some examples, once the user has selected one point, the GUI displays the range available for the second point based on the minimum and maximum imaging window size.

This minimum or maximum size is an inherent component of the imaging device in the radiotherapy device. The user selects a second point from the range displayed on the GUI to define the second edge of the imaging window.

Once the longitudinal edges of the imaging window have been marked on the GUI on the patient support, the patient support can ASU (automatic set-up), i.e. move automatically, to the centre of those makers, and set the imaging field size automatically. Alternatively the imaging device can automatically move and adjust to cover the imaging window.

In such scenarios the controller is configured to preform one of the following in response to receiving the user input: either adjust the position of the patient support system based on the location of the imaging window; or send instructions to adjust the position of an imaging device based on the location of the imaging window.

Thus, since the GIU is calibrated to the table itself, locations on the table can be selected and indicated. Locations on the table relevant to a radiotherapy treatment can be indicated and/or selected on the table itself.

In other examples the user could input other location information to the GUI, for example marking areas indicative of the present of absence of a patient, or marking an area on the table for other reasons.

In some embodiments it is possible that sensors are able to distinguish an authorised operative such as a medical operative versus an unauthorised operative or, for example, the patient to permit that the GUI only operates, displays to, receives inputs from, or responds to authorised operatives. This can be in any appropriate manner for example by virtue of the use of an appropriate identification element carried by the medical operative such as a short-range transmitter for example the pendant 306 shown in FIG. 3a.

It will be noted that the identification element can further provide location information in relation to the operative. This can be used to modify information sharing or other interaction with the operative both via the support surface GUI and through other interfaces as appropriate. For example, there may be multiple operatives in different locations. Where one operative is in a control room, another in a data transmission room, and a third at the patient support surface, the information, interaction and messages conveyed to and between each via the support surface GUI and otherwise can be modified accordingly.

The proximity sensors can be used to detect the presence of a user or objects in the vicinity of the patient support surface for the purpose of collision avoidance. For example, if the proximity detectors detect the presence of a user or object proximal to the table, movement of the support surface to that location may be modified based on the detection. In other examples, movement of other components of the radiotherapy device to that location may be modified. In some examples the controller may determine that the patient support surface or another component of the radiotherapy device will move to collide with or move to within a threshold distance of the detected object. The movement of the component is modified to avoid collision with the detected object. This could be in the form of rejecting any control instructions to move the table to a location in which an object has been detected, halting movement of the component, or recalculating movement of the component to avoid the detected object.

In operation, the radiotherapy device is operated in the conventional fashion up to the patient generally laying themselves on the support surface. Thereafter the operative will be guided by the GUI which will activate in their proximity. Various steps can be guided, for example the display can indicate how to position the patient by providing suitable instructions and/or indicating, by illuminating relevant regions, the desired position. This can be performed in conjunction, as appropriate, with patient position sensors to secure or otherwise accessorise the patient support surface and patient in a manner guided by the GUI, including instructions at the location of the operative as well as activation of portions of the GUI where specific steps need to be performed. As the operative moves around the table, corresponding sections will activate on the GUI to ensure that the operative does not have to move the display; instead the display follows the mover. In case of a fault, the GUI will indicate appropriately, and if the operative moves away then the GUI will deactivate.

If the sensors do not detect the presence of a user, this indicates that the user is absent. Thus the sensors can be used to detect user/operator absence. If the information from the sensors indicates that the operator is absent, the GIU is deactivated.

When the sensors detect that the operator is in the vicinity of the table, the GUI is active. When the operative moves away the sensors will no longer detect the presence of an operator in the vicinity of the table, indicating that the operator is absent. In response to this indication (operator absence), the GUI is deactivated.

In terms of the specific components of the GUI, any appropriate display can be used, for example a simple colour/lighting system if it is purely a matter of indicating where the operative should move to, a display screen carrying additional information and/or a touchscreen or other input interface permitting the operative to interact with the display to enter/seek additional information. Similarly, proximity sensing can be carried out in any appropriate manner for example by virtue of appropriate distance sensors such as infrared sensors, or by short distance detector sensors interacting with components carried by authorised operatives as appropriate. The proximity sensors can be integral with the display or located in any appropriate region on the patient support surface or any adjacent element such as a pedestal or base.

It will be seen that the approach provides significant benefit to the operative. Instead of having to move between the patient support surface and a separate display, the information is presented in the vicinity of the operative, simplifying the clinical workflow. Yet further the display can carry specific information permitting improved operation of the device, as well as carrying instructional or operational information ensuring that the clinical workflow including setting up procedures are performed in the correct order. Power consumption will be minimised by deactivating the GUI when the operative is not near, and additionally this can help avoid accidental use by the patient. As a result, the operative experience is improved by placing the interface close to the therapist whenever they are at the table.

Although the approach above is discussed in relation to a radiotherapy device of course it can be applied to any appropriate medical operating system, and can be executed by a processor operating under instructions stored in a computer readable medium.

The invention claimed is:

1. A patient support system for use with a medical device, comprising:
   a patient support surface comprising at least one electronic display region configured to display information;

one or more proximity sensors configured to provide one or more signals indicative of a presence of at least one of a person or object in a proximity of the patient support surface; and
   a controller configured to control information displayed on the at least one electronic display region based on the one or more signals received from the one or more proximity sensors, wherein the at least one electronic display region comprises a plurality of electronic display regions, and wherein the controller is further configured to:
      determine, based on the one or more signals received from the one or more proximity sensors, which electronic display region of the plurality of electronic display regions is nearest the person or object in a proximity to the patient support surface; and
      control the information displayed on the determined electronic display region based on the determination.

2. The patient support system as claimed in claim 1, wherein the controller is further configured to:
   cause the information to be displayed only on the determined electronic display region.

3. The patient support system of claim 1, wherein the controller is further configured to:
   deactivate the at least one electronic display region when no signal indicative of presence is provided to the controller by the one or more proximity sensors.

4. The patient support system of claim 1, wherein the one or more proximity sensors are configured to identify at least one of an authorized person or an authorized object and provide one or more signals indicative thereof or responsive thereto.

5. The patient support system of claim 1, wherein the controller is further configured to:
   display error or fault information.

6. The patient support system of claim 1, wherein the controller is configured to:
   display information based on a subsequent step in at least one of a clinical, service or a physics workflow.

7. The patient support system of claim 6, wherein the subsequent step comprises performing a step in relation to the patient support surface, and wherein the displayed information at least one of indicates or is displayed at a location where the subsequent step requires performance.

8. The patient support system of claim 6, wherein the subsequent step comprises attaching an accessory to the patient support surface via one or more attachment members located on the patient support surface, and wherein the displayed information indicates the location of the one or more attachment members.

9. The patient support system of claim 6, wherein the subsequent step comprises indicating via the at least one electronic display region, patient positioning information.

10. The patient support system of claim 1, wherein the controller is further configured to:
   control at least one of an MR imaging apparatus, an RT apparatus, or a subject support surface.

11. The patient support system of claim 1, wherein the at least one electronic display region further comprises an input interface.

12. The patient support system of claim 11, wherein the input interface comprises at least one of a touch screen, microphone or keyboard.

13. The patient support system of claim 11, wherein the at least one electronic display region is a touchscreen, and wherein the controller is configured to receive a user input via the touchscreen, the user input indicating a location of an imaging window on the patient support surface for a radiotherapy treatment.

14. The patient support system of claim 13, wherein the controller is configured to, in response to the user input, perform one of:

adjust a position of the patient support system based on the location of the imaging window; or send instructions to adjust a position of an imaging device based on the location of the imaging window.

15. The patient support system of claim 13, where the user input is received at a location aligning with an edge of the imaging window in the patient support surface.

16. The patient support system of claim 1, further including:

one or more additional sensors configured to detect an alarm-indicating action by a patient.

17. The patient support system of claim 1, further comprising:

an identification element detector configured to detect at least one of a proximity or a location of an identification element.

18. The patient support system of claim 1, wherein at least one of the at least one electronic display region, the one or more proximity sensors, or the controller are configured to deactivate in case of operator absence.

19. A method of controlling a patient support system electronic display region, the method comprising:

receiving a signal from a proximity sensor, the signal being indicative of a presence of at least one of a person or an object in a proximity to a patient support surface; and controlling information displayed on the electronic display region based on the signal received from the proximity sensor, wherein the electronic display region comprises one of a plurality of electronic display regions, and wherein controlling information displayed on the plurality of electronic display regions comprises:

determining, based on the signal received from the proximity sensor, which electronic display region of the plurality of electronic display regions is nearest to the person or the object in proximity to the patient support surface; and controlling the information displayed on the determined electronic display region based on the determination.

20. The method as claimed in claim 19, further comprising:

displaying information in a proximity of at least one of a detected person or a detected object.

21. The method of claim 19, further comprising:

deactivating the electronic display region when a person or an object presence is not sensed.

22. The method of claim 19, further comprising at least one of:

displaying information in the electronic display region relating to a subsequent step in a clinical workflow;

indicating, at an area of the electronic display region adjacent a location for addition of an accessory, instructions or other indications in relation to attaching the accessory; or controlling operation of at least one of an MR imaging apparatus, an RT apparatus, or a subject support surface via the electronic display region.

23. The method of claim 19, wherein the electronic display region comprises a touchscreen, and wherein the method further comprises:

receiving, via the touchscreen, a user input indicative of a location of an imaging window for a radiotherapy treatment, wherein the user input is received at a location aligning with an edge of the imaging window in the patient support surface, and in response to the user input, performing at least one of:

adjusting a position of the patient support system based on the location of the imaging window; or sending an instruction to adjust a position of an imaging device based on the location of the imaging window.

24. A non-transitory computer readable medium with instructions stored thereon, which when executed by a processor of a computer, cause the processor to:

receive a signal from a proximity sensor, the signal being indicative of a presence of at least one of a person or an object in proximity to a patient support surface; and control information displayed on at least one electronic display region based on the signal received from the proximity sensor, wherein the at least one electronic display region comprises one of a plurality of electronic display regions, and wherein controlling information displayed on the plurality of electronic display regions comprises:

determining, based on the signal received from the proximity sensor, which electronic display region of the plurality of electronic display regions is nearest to the person or the object in proximity to the patient support surface; and controlling the information displayed on the determined electronic display region based on the determination.

\* \* \* \* \*